United States Patent

Baswell et al.

[11] Patent Number: 4,704,126
[45] Date of Patent: Nov. 3, 1987

[54] CHEMICAL POLISHING PROCESS FOR TITANIUM AND TITANIUM ALLOY SURGICAL IMPLANTS

[75] Inventors: Imogene Baswell; Kimberly Walsh; Eric Benz, all of Memphis, Tenn.

[73] Assignee: Richards Medical Company, Memphis, Tenn.

[21] Appl. No.: 723,098

[22] Filed: Apr. 15, 1985

[51] Int. Cl.⁴ .......................... A61F 2/18; A61F 2/04
[52] U.S. Cl. ......................................... 623/10; 123/12
[58] Field of Search ................ 134/41, 3, 32; 623/10, 623/66, 16, 22, 11, 12; 128/92 R, 926

[56] References Cited

U.S. PATENT DOCUMENTS

| | | | |
|---|---|---|---|
| 2,942,954 | 6/1960 | Thomas | 41/42 |
| 2,981,609 | 4/1961 | Acker et al. | 134/41 X |
| 3,514,407 | 5/1970 | Missel | 134/41 X |
| 3,562,013 | 2/1971 | Mickelson et al. | 134/3 |
| 3,605,123 | 9/1971 | Hahn | 623/16 |
| 3,725,224 | 4/1973 | Kendall | 204/141.5 |
| 3,749,618 | 7/1973 | Fannin et al. | 156/3 |
| 3,891,456 | 6/1975 | Hohman et al. | 134/3 |
| 4,075,040 | 2/1978 | Villain | 134/41 X |
| 4,169,292 | 10/1979 | Grote | 623/16 X |
| 4,170,488 | 9/1979 | Norman | 134/32 X |

OTHER PUBLICATIONS

"Low Temperature Creep of Ti-6 Al-4 V" by Ben C. Odegard and Anthony W. Thompson, Metallurgical Transactions, Apr. 1974.

Primary Examiner—Richard J. Apley
Assistant Examiner—Alan W. Cannon
Attorney, Agent, or Firm—Pravel, Gambrell, Hewitt, Kimball & Krieger

[57] ABSTRACT

A method of chemically polishing medical implants by immersing them in a solution including lactic acid, hydrofluoric acid, and nitric acid to produce smooth, matte finished implants.

9 Claims, 3 Drawing Figures

CHEMICAL POLISHING PROCESS FOR TITANIUM AND TITANIUM ALLOY SURGICAL IMPLANTS

BACKGROUND OF THE INVENTION

The invention relates to a method of chemically polishing medical implants made of titanium or an alloy of titanium to produce a smooth, matte finished surface.

Chemically pure titanium and Ti-6Al-4V alloy are extremely biocompatible materials which are used for a variety of medical applications including implants. When an implant fabricated from such a metal is implanted in the human body, the host tissue surrounding the implant fixes itself to the implant in direct apposition to the implant, in contrast with other common implant materials to which fibrous tissue may tend to encapsulate the implant. Thus titanium and alloys thereof are particularly useful for implants in which the former direct apposition type of fixation is preferable to the later surrounding type of fixation.

If a titanium implant surface is rough, tissue will attach itself mechanically at the implant-tissue interface. Although for a permanent implant, this type of fixation may be appropriate in that it is a predictable stabilizing mechanism, for a semi-permanent (long-term temporary) implant, such permanent fixation is undesirable. When the implant is to be removed, it may be necessary to cut the implant from the surrounding tissue thus creating trauma to the surrounding tissue. Examples of implants intended for temporary or semi-permanent implantation include ventilation tubes, e.g. a vent tube for the tympanic membrane, percutaneous devices for drug infusion, and other similar devices. The invention is particularly suitable for implants having intricate designs and/or of small size which are difficult to polish by conventional metal polishing techniques and for implants designed to create a passageway through surrounding tissue, where tissue ingrowth may clog the passageway decreasing its effectiveness for ventilation and/or fluid drainage.

A further problem with rough or sharp edges on implants is that they may cause an undesirable inflammatory response by surrounding body tissue. A smooth surface is also required for articulating implants, or implants that come in direct contact with blood. For these reasons, among others, such implants should be polished in some manner after they are fabricated.

In the past, metal implants have been finished by a variety of techniques including hand polishing, glass beading, vapor blasting, and electrolytic polishing. Although acceptable for many applications, it is difficult to effectively polish all surfaces and crevices of miniature implants, or implants having intricate designs and/or internal passageways. Mechanical polishing and electrolytic polishing produce a finished product having a bright, light-reflective surface. This type of surface is undesirable because bright light used for inserting the implant can cause considerable glare which interferes with the physician's ability to see the exact location of the implant. Thus it would be desirable to have a polishing technique which reduces glare and is more effective in polishing internal passageways as well as external surfaces of multi-faceted implants and instruments.

SUMMARY OF THE INVENTION

The invention relates to a method of chemically polishing surgical implants formed of titanium or titanium alloys such as Ti-6Al-4V which produces a smooth, matte finished implant. The invention includes contacting the formed implant with a polishing solution including lactic acid or glycerine, hydroflouric acid, and nitric acid; moving the solution and implant relative to one another; and thereafter washing the implant to remove the polishing solution and stop the polishing action.

The polishing solution preferably includes from about 60 to about 79 weight percent lactic acid, from about 10.5 to about 20 weight percent hydroflouric acid, and from about 10.5 to about 20 weight percent nitric acid. For polishing several implants in a batch polishing process, it is preferred that the polishing be accomplished in a series of immersing and washing steps, with inspection of the polished implants after each polishing stage to determine the extent of polishing and prevent over-polishing or too much metal removal for any single implant.

By practicing the instant invention, surgical implants formed of titanium or titanium alloys can be successfully polished to minimize tissue fixation normally associated with rough surfaced implants, minimize clogging of interior passageways, and substantially prevent reflective glare from interfering with the surgical implantation procedure.

BRIEF DESCRIPTIONS OF THE DRAWINGS

DETAILED DESCRIPTION OF A PREFERRED EMBODIMENT

The method of the present invention can be used for any titanium or titanium alloy surgical implant which is used for medical applications. For implants such as drainage or ventilation tubes and the like, for example ossicular replacement prostheses and middle ear ventilation tubes having intricate and miniature designs, the chemical polishing method of the instant invention provides both more effective polishing than mechanical methods previously used and a matte finish which substantially prevents undesirables glare during the implantation procedure.

Although chemical polishing in accordance with the instant invention may impart hydrogen ions to the surface of the implant or instrument, and thus may create hydrogen embrittlement, residual hydrogen ions can be removed by heating the implant or instrument to a particular temperature, depending on the dimensions and anticipated loading of the part to drive off the hydrogen ions. For this reason, it is believed that the chemical polishing of the instant invention is suitable for most, if not all, implants and instruments for which the matte finish and effective polishing of intricate designs is desirable.

The following discussion of the method of the instant invention is directed to chemically polishing middle ear vent tubes used for insertion in a myringotomy procedure which involves making an incision or slit in the eardrum to alleviate a build-up of fluid caused by negative pressure in the middle ear cavity—a condition known as otitis media. The tube primarily keeps the ear drum slit open for a sufficient period of time following the surgery to allow fluid to drain and the middle ear cavity to dry out and to equalize pressure between the middle and the outer ear area. Frequently the condition of middle ear fluid or pressure imbalance in the middle ear cavity which the tube is intended to alleviate requires that the tube remain in place for a significant period of time. However, when the otitis media condition is no longer present, the purpose of the ear tube no longer exists and should be removed. In the majority of cases, ventilation tubes will extrude naturally due to the rotation and sloughing of tympanic membrane tissue. An ear vent tube polished using the chemical polishing process of the instant invention will have less tendency to be fixed permanently and will be less likely to resist natural extrusion.

Although the following example relates to polishing a particular size of middle ear ventilation tubes, as can be appreciated, the method of the present invention is not so limited and can be used for any type of titanium or titanium alloy implant.

Figure 3:
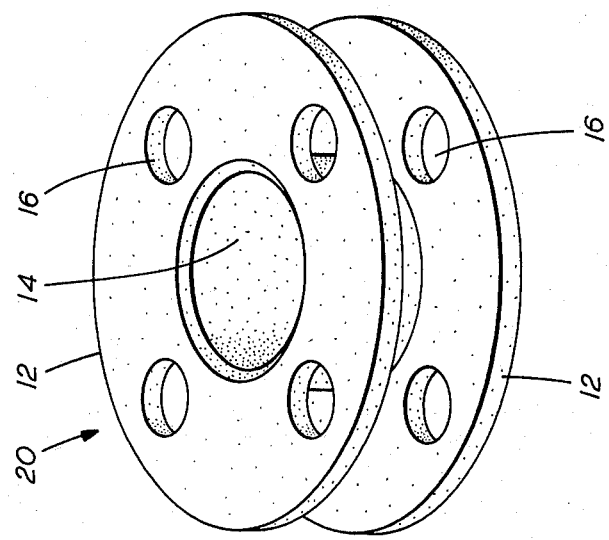
FIG. 3 is a Reuter bobbin polished in accordance with the instant invention.
Figure 2:
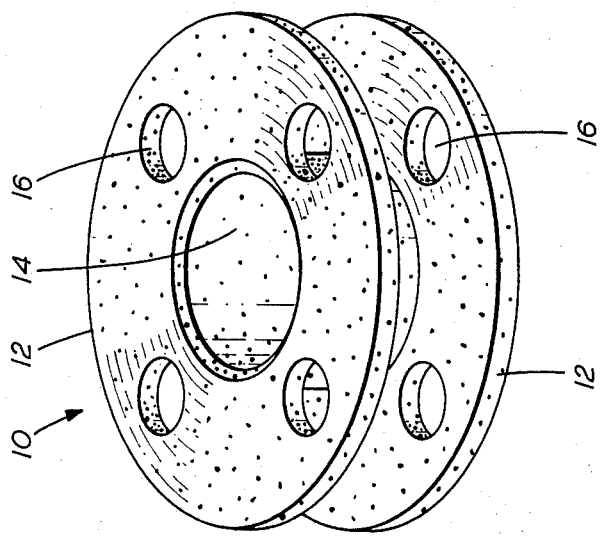
FIG. 2 is a Reuter bobbin polished using prior art vapor blasting technique.

In the following examples, the middle ear vent tubes polished in accordance with the instant invention were Reuter bobbins, e.g. bobbin 10 of FIG. 1, manufactured by Richards Medical Company sold as Catalog No. 14-5219. FIG. 2 shows the bobbin 10 polished using the prior art vapor blasting technique. FIG. 3 shows the smooth, matte finished bobbin 20 polished in accordance with the instant invention.

Figure 1:
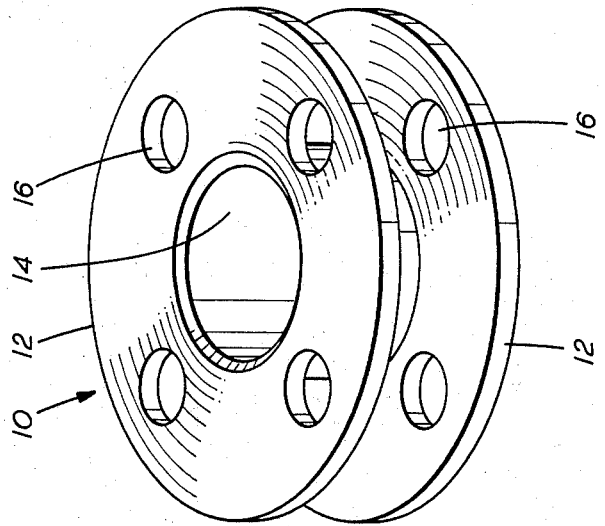
FIG. 1 is a photograph of a Reuter bobbin as machined, prior to practicing the instant invention.

The bobbin 10, shown in FIG. 1, was machined from a single piece of Ti-6Al-4V to include flanges 12 and lumen 14. Each of the flanges 12 included holes 16. Before polishing, the inside diameter of the lumen 14 was about 0.0389 inches (1.0 mm), the outside diameter of each of the flanges 12 was 0.1099 inches (2.8 mm), each of the flanges were about 0.0105 inches (0.27 mm) thick, and the flange holes 16 each had an inside diameter of about 0.0167 inches (0.42 Mm).

The polishing solution used in the following example included one part hydrofluoric acid, one part nitric acid, and three parts lactic acid. Due to the corrosive effect of hydroflouric acid on glass, a polyethylene container for the polishing solution bath was constructed having a volume of approximately 425 milliliters. A basket to enclose the ear vent tubes was constructed from type 304 stainless steel mesh (50 mesh, 0.010 inches in diameter) and wire, having overall dimensions of approximately 1½ inch by 1½ inch by ¾ inch deep (3.8 cm×3.8 cm×1.9 cm). The polishing was accomplished by submerging the wire basket containing thirty of the bobbins 10, and agitating the bobbins within the container of polishing solution by slowly moving the wire basket across the bottom of the polyethylene container of solution.

Because the depth of machining grooves and other imperfections on the individual bobbins vary, a single immersion did not produce uniform polishing of all of the bobbins. For this reason, successive polishing steps were found to be preferable to a single, longer immersion for achieving uniformly polished bobbins.

For the above described middle ear vent tubes, it was found that good polishing resulted from first cleaning the batch of implants in acetone and drying with heat before polishing. An initial polishing step consisted in immersing the implants for 5 seconds with mild agitation followed by washing them in clear water with agitation, and again cleaning with acetone and drying. This preliminary polishing step serves to prevent overpolishing by restricting the time in the polishing solution. A second polishing step including 10 second immersion and agitation in the polishing compound followed by washing and drying is preferred to permit satisfactorily polished bobbins to be removed after inspection. As noted above, due to the varying depths of machine lines, some bobbins with machine grooves of relatively shallow depth will be completely polished after this step. These polished bobbins are removed from the batch, and the process of ten second polishing, followed by cleaning and inspecting is repeated until all of the remaining bobbins are polished.

It is preferred for the bobbins described above that the maximum chemical polishing time not exceed 65 seconds to keep the polished bobbin within production specification dimensions, and that the final water rinse should be 10 minutes to assure complete removal of the polishing compound to prevent overpolishing.

Practicing the particular technique outlined with a batch of 30 bobbins, as illustrated by Table I below, resulted in very little metal removal, with the mean difference in bobbin dimensions being no more than 0.0017 inches (0.043 mm). The standard deviations in dimension differed by no more that 0.0001 inches (0.003 mm). Thus the polished bobbins were maintained within production specifications for dimensions.

TABLE I

| Measurements Before and After the Chemical Polishing of 30 Reuter Bobbin Vent Tubes* | | | |
|---|---|---|---|
| | Before (n = 30) | After (n = 28) | Difference |
| I.D. of Lumen (A) | = 0.0389 | = 0.0399 | = 0.0010 |
| | = 0.0004 | = 0.0005 | = 0.0001 |
| O.D. of Flange (B) | = 0.1099 | = 0.1091 | = 0.0008 |
| | = 0.0006 | = 0.0007 | = 0.0001 |
| Flange Thickness (C) | = 0.0105 | = 0.0095 | = 0.0010 |
| | = 0.0006 | = 0.0006 | = 0.0000 |
| Flange Hole Diameter (D) | = 0.0167 | = 0.0184 | = 0.0017 |
| | = 0.0005 | = 0.0004 | = 0.0001 |

*Units are in inches

The results shown in Table I represent 30 bobbins subjected to repetitive immersions of 5 seconds, 10 seconds, 10 seconds, 20 seconds, and then 20 seconds, with satisfactorily polished bobbins being removed after inspection at various stages from just after the first 10 second immersion through after the last 20 second immersion. As can be appreciated, metal removed from bobbins remains in the polishing solution so that successive immersions require somewhat more time to achieve the same amount of metal removal as preceeding immersions.

The chemical polishing process of the instant invention provides a polishing technique which produces a smooth, matte finished implant or instrument in very little time with very little labor which is particularly suitable for small titanium or titanium alloy parts. Although the discussion was directed to polishing bobbins or ear vent tubes, the invention is not limited to such implants, and can be readily adapted to many types of medical products for which a smooth, matte finish is desirable.

The foregoing disclosure and description of the invention are illustrative and explanatory thereof, and various changes in the size, shape and materials, as well as in the details of the illustrated construction may be made without departing from the spirit of the invention.

What is claimed is:

1. A method of polishing a surgical ear tube implant formed of a biocompatible titanium or titanium alloy having a smooth polished surface that discourages tissue growth thereon, comprising the steps of:
   a. contacting the implant with a polishing solution including lactic acid, hydrofluoric acid and nitric acid;
   b. moving the implant and polishing compound relative one to the other; and thereafter
   c. washing the implant to remove substantially all of the polishing compound until the alloy has matte finish.

2. The method of claim 1 wherein the contacting step includes immersing the implant in a polishing solution that comprises:
   from about 60 to about 79 weight percent lactic acid;
   from about 10.5 to about 20 weight percent hydroflouric acid; and
   from about 10.5 to about 20 weight percent nitric acid.

3. The method of claim 1, wherein the moving step includes agitating the immersed implant in the solution.

4. The method of claim 1 wherein the contacting and moving steps are carried out long enough to effectively remove surface irregularities on the implant without removing excessive amounts of the implant material.

5. The method of claim 3 wherein the washing step is followed by the step of inspecting the polished implant to determine the extent of polishing and thereafter repeating the contacting, moving, and washing steps if more polishing is needed.

6. A polished surgical ear tube implant comprising an ear tube surgical implant formed of a biocompatible titanium or titanium alloy polished to a smooth, matte finish by contacting the formed implant with a polishing solution including lactic acid, hydrofluoric acid, and nitric acid;
   a. moving the implant and solution relative to one another; and thereafter
   b. washing the implant to remove substantially all of the polishing solution to produce the polished implant.

7. The polished ear tube implant of claim 6 wherein the polishing solution comprises:
   from about 60 to about 79 weight percent lactic acid;
   from about 10.5 to about 20 weight percent hydroflouric acid; and
   from about 10.5 to about 20 weight percent nitric acid.

8. The polished ear tube implant of claim 7 wherein the immersed implant is polished by agitating the immersed implant in the solution.

9. The polished ear tube implant of claim 8 wherein the formed implant is an ear tube having machining grooves therein and wherein the contacting, moving, and washing steps are repeated to substantially decrease the depth of the grooves to produce a smooth, matte finished ear tube.

* * * * *